United States Patent
Cullen et al.

(10) Patent No.: US 9,669,172 B2
(45) Date of Patent: Jun. 6, 2017

(54) DISCREET RESPIRATORY THERAPY SYSTEM

(71) Applicant: ResMed Limited, Bella Vista (AU)

(72) Inventors: Christopher Samuel Cullen, Lane Cove (AU); Damien Julian Mazzone, Concord West (AU); Muditha Pradeep Dantanarayana, Cherrybrook (AU); Tumul Gupta, Bligh Park (AU); Justin John Formica, Voyager Point (AU); Aaron Samuel Davidson, Mona Vale (AU)

(73) Assignee: ResMed Limited (AU)

( * ) Notice: Subject to any disclaimer, the term of this patent is extended or adjusted under 35 U.S.C. 154(b) by 559 days.

(21) Appl. No.: 13/934,596

(22) Filed: Jul. 3, 2013

(65) Prior Publication Data

US 2014/0020687 A1    Jan. 23, 2014

Related U.S. Application Data

(60) Provisional application No. 61/668,149, filed on Jul. 5, 2012.

(51) Int. Cl.
*A61M 16/00* (2006.01)
*A61M 16/06* (2006.01)
(Continued)

(52) U.S. Cl.
CPC .... *A61M 16/0066* (2013.01); *A61M 16/0051* (2013.01); *A61M 16/0057* (2013.01);
(Continued)

(58) Field of Classification Search
None
See application file for complete search history.

(56) References Cited

U.S. PATENT DOCUMENTS 1,848,232 A * 3/1932 Swope ............... A61M 16/00
128/205.23
3,717,147 A * 2/1973 Flynn ............... A61M 16/127
128/204.25
(Continued)

FOREIGN PATENT DOCUMENTS

EP    0512285 A1    11/1992
EP    0825103 A2    2/1998
(Continued)

OTHER PUBLICATIONS

Teledyne Hastings Instruments, "Instructional Manual, 201/203/205/207 Series Flow Meters/Controllers", Jul. 2011, retrieved from http://www.teledyne-hi.com/Manual/Flow/141-HFM-201_HFC-203_Manual.pdf. (as submitted by Applicant in IDS dated Oct. 7, 2014).*
(Continued)

*Primary Examiner* — (Jackie) Tan-Uyen T Ho
*Assistant Examiner* — Joseph D Boecker
(74) *Attorney, Agent, or Firm* — Lerner, David, Littenberg, Krumholz & Mentlik, LLP

(57) ABSTRACT

A device provides respiratory treatment such as for sleep disordered breathing and other respiratory conditions in a discreet configuration to provide a minimally invasive system. The system may include a flow pressurizer apparatus configured to generate a pressurized flow of air through a fine bore delivery conduit toward a patient interface. The system may further include a treatment compensator coupled with the fine bore delivery conduit. The treatment compensator may be configured at the patient interface to reduce pressure for patient inspiration. A processor may control adjustments to the pressure generated by the flow pressurizer apparatus.

30 Claims, 8 Drawing Sheets

(51) Int. Cl.
*A61M 16/08* (2006.01)
*A61M 16/12* (2006.01)
*A61M 16/20* (2006.01)
*A61M 16/10* (2006.01)
*A61M 16/16* (2006.01)

(52) U.S. Cl.
CPC ........ *A61M 16/0063* (2014.02); *A61M 16/06* (2013.01); *A61M 16/0666* (2013.01); *A61M 16/0816* (2013.01); *A61M 16/0875* (2013.01); *A61M 16/1005* (2014.02); *A61M 16/12* (2013.01); *A61M 16/127* (2014.02); *A61M 16/20* (2013.01); *A61M 16/204* (2014.02); *A61M 16/209* (2014.02); *A61M 16/0069* (2014.02); *A61M 16/0683* (2013.01); *A61M 16/0866* (2014.02); *A61M 16/109* (2014.02); *A61M 16/16* (2013.01); *A61M 16/201* (2014.02); *A61M 2016/0021* (2013.01); *A61M 2016/0027* (2013.01); *A61M 2016/0039* (2013.01); *A61M 2205/21* (2013.01); *A61M 2205/3344* (2013.01); *A61M 2205/3355* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/75* (2013.01)

(56) References Cited

U.S. PATENT DOCUMENTS

| | | | | |
|---|---|---|---|---|
| 3,906,996 | A | 9/1975 | DePass et al. | |
| 4,393,869 | A | 7/1983 | Boyarsky et al. | |
| 5,036,847 | A * | 8/1991 | Boussignac | A61M 16/127 128/203.12 |
| 5,245,995 | A | 9/1993 | Sullivan et al. | |
| 5,485,850 | A * | 1/1996 | Dietz | A61B 6/541 128/204.23 |
| 5,676,342 | A | 10/1997 | Otto et al. | |
| 5,704,354 | A | 1/1998 | Preidel et al. | |
| 5,752,506 | A * | 5/1998 | Richardson | A61M 16/0096 128/204.18 |
| 5,794,614 | A * | 8/1998 | Gruenke | A61M 16/00 128/202.22 |
| 6,253,764 | B1 * | 7/2001 | Calluaud | A61M 16/20 128/204.18 |
| 6,279,574 | B1 * | 8/2001 | Richardson | A61M 16/0096 128/204.17 |
| 6,349,724 | B1 * | 2/2002 | Burton | A61M 16/0057 128/204.18 |
| 6,354,291 | B1 | 3/2002 | Brown et al. | |
| 6,363,933 | B1 | 4/2002 | Berthon-Jones | |
| 6,398,739 | B1 | 6/2002 | Sullivan et al. | |
| 6,401,714 | B1 | 6/2002 | Giorgini | |
| 6,435,032 | B1 | 8/2002 | Holloway et al. | |
| 6,615,831 | B1 | 9/2003 | Tuitt et al. | |
| 6,634,356 | B1 | 10/2003 | O'Dea et al. | |
| 6,635,021 | B1 | 10/2003 | Sullivan et al. | |
| 6,770,037 | B2 | 8/2004 | Sullivan et al. | |
| 6,886,591 | B2 | 5/2005 | Jennings | |
| 7,004,908 | B2 | 2/2006 | Sullivan et al. | |
| 7,080,645 | B2 | 7/2006 | Genger et al. | |
| 7,080,660 | B2 | 7/2006 | Jennings | |
| 7,141,021 | B2 | 11/2006 | Sullivan et al. | |
| 7,314,046 | B2 | 1/2008 | Schroeder et al. | |
| 7,331,345 | B2 | 2/2008 | Haston | |
| 7,748,683 | B1 | 7/2010 | Kelly | |
| 7,931,023 | B2 * | 4/2011 | Berthon-Jones | A61M 16/00 128/204.18 |
| 8,011,380 | B2 | 9/2011 | Califano et al. | |
| 8,025,053 | B1 | 9/2011 | Prete et al. | |
| 8,166,974 | B2 | 5/2012 | Pedemonte | |
| 8,215,336 | B2 | 7/2012 | Jennings | |
| 8,365,728 | B2 | 2/2013 | Hamilton et al. | |
| 2003/0015200 | A1 * | 1/2003 | Hansen | A61M 16/00 128/204.18 |
| 2003/0192543 | A1 * | 10/2003 | Arnott | A61M 16/06 128/204.18 |
| 2003/0209246 | A1 * | 11/2003 | Schroeder | A61M 16/0808 128/204.17 |
| 2006/0011198 | A1 * | 1/2006 | Matarasso | A61M 16/06 128/204.18 |
| 2006/0180149 | A1 * | 8/2006 | Matarasso | A61M 16/06 128/204.18 |
| 2008/0078395 | A1 * | 4/2008 | Ho | A61M 16/208 128/205.24 |
| 2009/0044807 | A1 * | 2/2009 | Boussignac | A61M 16/04 128/205.25 |
| 2009/0151728 | A1 * | 6/2009 | McConnell | A61M 16/107 128/206.19 |
| 2010/0326533 | A1 | 12/2010 | Mooney et al. | |
| 2011/0094518 | A1 | 4/2011 | Cipollone et al. | |
| 2012/0298108 | A1 * | 11/2012 | Kane | A61M 16/0051 128/204.23 |
| 2012/0304993 | A1 * | 12/2012 | Nitta | A61M 16/0072 128/204.18 |
| 2013/0074842 | A1 * | 3/2013 | Boucher | A61M 16/16 128/203.16 |
| 2013/0269693 | A1 * | 10/2013 | Neatrour | A61M 16/0051 128/203.12 |
| 2015/0335851 | A1 * | 11/2015 | Cullen | A61M 16/0066 128/204.25 |

FOREIGN PATENT DOCUMENTS

| | | |
|---|---|---|
| EP | 1318307 A1 | 6/2003 |
| EP | 1655052 A2 | 5/2006 |
| EP | 1484242 B2 | 11/2010 |
| JP | 10-132137 | 5/1998 |
| WO | 0043060 A1 | 7/2000 |
| WO | 0066920 A1 | 11/2000 |
| WO | 2011089491 A1 | 7/2011 |
| WO | 2012156885 A1 | 11/2012 |
| WO | 2013040198 A2 | 3/2013 |

OTHER PUBLICATIONS

Bronkhorst USA, Control Valves, Dec. 2011, <http://www.bronkhorstusa.com/en/products/control_valves/>.

Emerson Industrial Automation, Proportional Valves, 8202 / 8203 Series, Copyright 2013, <http://www.ascovalve.com/Applications/Products/ProportionalControl.aspx>.

Equilibar Precision Pressure Control, Equilibar Back Pressure Regulator, Jun. 2011,<http://www.equilibar.com/back-pressure-regulator/introduction.asp>.

International Search Report and Written Opinion for Application No. PCT/AU2013/000737 dated Sep. 26, 2013.

Parker, Miniature Proportional Valves, VSO Series, Feb. 2013, <http://www.parker.com/literature/Literature%20Files/Precision%20Fluidics%20Division/UpdatedFiles/PPF_Proportional_Catalog.pdf>.

South Bend Controls, Proportional Flow Control Valves Servoid, Aug. 2012,<http://www.sbcontrols.com/products.aspx/proportional-flow-control-valves>.

Teledyne Hastings Instruments, Instructional Manual, 201/203/205/207 Series Flow Meters/Controllers, Jul. 2011, <http://www.teledyne-hi.com/Manual/Flow/141-HFM-201_HFC-203_Manual.pdf>.

The Clippard Valve Equilibar, Proportional Valves, EVP Series Proportional Valves, Oct. 2012,<http://www.clippard.com/products/electronic-valve-proportional>.

Written Opinion of the International Preliminary Examination Authority for Application No. PCT/AU2013/000737 dated Jul. 4, 2014.

Partial Search Report for Application No. PCT/AU2013/000737 dated Aug. 20, 2013.

(56) References Cited

OTHER PUBLICATIONS

Hastings Instruction Manual, "201/203 Series Flowmeters/Controllers", Aug. 2002.
Respironics, "WhisperFlow: CPAP system—Variable & Fixed User's Manual", Copyright 2008.
Wong et al., "Use of venturi entrainment to deliver nasal high flow oxygen", Crit Care & Shock (2010), vol. 13, No. 3, pp. 75-80.
European Search Report for Application No. EP13813497 dated Dec. 21, 2015.

* cited by examiner

DISCREET RESPIRATORY THERAPY SYSTEM

CROSS REFERENCE TO RELATED APPLICATIONS

This application claims the benefit of the filing date of U.S. Provisional Patent Application No. 61/668,149 filed Jul. 5, 2012, the disclosure of which is hereby incorporated herein by reference.

FIELD OF THE TECHNOLOGY

The present technology relates to methods and apparatus for treatment of respiratory conditions such as the conditions related to sleep disordered breathing (SDB) (including mild obstructive sleep apnea (OSA)), allergy induced upper airway obstruction or early viral infection of the upper airway.

BACKGROUND OF THE TECHNOLOGY

Sleep is important for good health. Frequent disturbances during sleep or sleep fragmentation can have severe consequences including day-time sleepiness (with the attendant possibility of motor-vehicle accidents), poor mentation, memory problems, depression and hypertension. For example, a person with nasal congestion may snore to a point that it disturbs that person's ability to sleep. Similarly, people with SDB are also likely to disturb their partner's sleep. One known effective form of treatment for patients with SDB is nasal continuous positive airway pressure (nasal CPAP) applied by a flow generator (e.g., a servo-controlled blower via a connecting hose and patient interface. In some forms the supply of air at positive pressure is delivered to both the nose and mouth, such as with a mask. The positive pressure can prevent a collapse of the patient's airway during inspiration, thus preventing events such as snoring, apnoeas or hypopnoeas and their sequelae.

Such positive airway pressure may be delivered in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly change with the patient's breathing cycle. A pressure setting during expiration lower than inspiration may generally be referred to as expiratory pressure relief. An automatically adjusting device may increase the treatment pressure in response to indications of partial or complete upper airway obstruction or other sleep disordered breathing events. See U.S. Pat. Nos. 5,245,995; 6,398,739; 6,635,021; 6,770,037; 7,004,908; 7,141,021; 6,363,933 and 5,704,345. Treatment pressure produced by such CPAP devices typically range from 4 cm $H_2O$ to 22 cm $H_2O$ for treatment of OSA, depending on patient requirements. Treatment pressures for assisted ventilation can range of up to 32 cm $H_2O$.

Other devices are known for providing respiratory tract therapy. For example, Schroeder et al. describes an apparatus for delivering heated and humidified air to the respiratory tract of a human patient in U.S. Pat. No. 7,314,046, which was filed on 8 Dec. 2000 and assigned to Vapotherm Inc. Similarly, Genger et al. discloses an anti-snoring device with a compressor and a nasal air cannula in U.S. Pat. No. 7,080,645, filed 21 Jul. 2003 and assigned to Seleon GmbH.

It may be desirable to develop further methods and devices for treating respiratory conditions.

SUMMARY OF THE TECHNOLOGY

A first aspect of some embodiments of the technology is to provide methods and apparatus for directing pressurized air to a user or patient for a respiratory treatment of respiratory conditions.

Another aspect of some embodiments of the technology is to provide methods and apparatus for treating sleep disordered breathing.

A further aspect of some embodiments is to provide components of such technology with a configuration to improve comfort and patient compliance.

A still further aspect of some embodiments of such technology is to provide a system with minimal invasiveness.

In some embodiments of the technology, breathable gas may be directed toward an interface of a user or patient by implementation of fine bore delivery conduit.

Some embodiments of the present technology relate to a respiratory treatment system. The system may include a flow pressurizer apparatus configured to generate a pressurized flow of air through a fine bore delivery conduit toward a patient interface. The system may further include a treatment compensator coupled with the fine bore delivery conduit and configured at the patient interface to reduce the first pressure for patient inspiration to a second pressure above atmospheric pressure. The system may further include a processor configured to control adjustments to the first pressure generated by the flow pressurizer apparatus.

In some cases, the flow pressurizer apparatus may include a compressor configured to generate the pressurized flow of air. The flow pressurizer apparatus may include a step-up flow generator. Optionally, the flow pressurizer apparatus may further include a foundational flow generator. The foundational flow generator may be coupled with the step-up flow generator by a large bore delivery conduit.

In some cases, the system may include a Venturi chamber coupled to the patient interface. The Venturi chamber may be configured to entrain atmospheric air proximate to a nozzle coupled with an output of the fine bore delivery conduit. The system may also include a foam filter configured at an entrainment inlet of the Venturi chamber.

In some versions, the treatment compensator may include a pressure step-down chamber including a shuttle configured to move to reduce the first pressure at an input to the step-down chamber to the second pressure at an output of the step-down chamber. The shuttle may be activated by an air feed-back passage.

In some cases, the treatment compensator may include a stint valve configured to selectively reduce a flexible passage of the treatment compensator to reduce the first pressure for patient inspiration. The stint valve may include a solenoid actuator controlled by the processor as a function of a measure of pressure from a pressure sensor located proximate to an output of the stint valve. The stint valve may include an actuation lever. The lever may be configured proximate to a pressure feedback chamber having a membrane. Such a membrane may be configured to move the lever with changing pressure of the pressure feedback chamber.

In some cases, the stint valve may include first and second pressure activation chambers adjacent to first and second membranes of the flexible passage. The first pressure activation chamber may be a feed-forward pressure chamber in gas communication with an input side of the flexible passage. The second pressure activation chamber may be a feedback pressure chamber in gas communication with an output side of the flexible passage. The first pressure activation chamber may include a release vent having a release vent gate.

In some cases, the system may further include a gas source input configured to couple with a supplemental oxygen gas source such that the input is configured to direct the supplemental oxygen to mix with the pressurized air.

Some embodiments of the present technology may relate to a method for control of a respiratory treatment apparatus. The method may include producing with a flow pressurizer system a flow of air through a fine bore tube toward a patient interface at a first pressure above atmospheric pressure. The method may further include compensating at the patient interface with a treatment compensator to reduce the first pressure for patient inspiration to a second pressure above atmospheric pressure. The method may also include controlling with a processor adjustments to the first pressure generated by the flow pressurizer system.

In some cases, the flow pressurizer apparatus may include a compressor configured to generate the pressurized flow of air. The flow pressurizer apparatus may include a step-up flow generator. The flow pressurizer apparatus may further include a foundational flow generator. The foundational flow generator may be coupled with the step-up flow generator by a large bore delivery conduit.

In some cases, the method may further include entraining atmospheric air with a Venturi chamber coupled to the patient interface such that entraining may be proximate to a nozzle coupled with an output of the fine bore delivery conduit. The entraining may be performed through a foam filter configured at an entrainment inlet of the Venturi chamber.

In some such cases, the treatment compensator may include a pressure step-down chamber including a shuttle moving to reduce the first pressure at an input to the step-down chamber to the second pressure at an output of the step-down chamber such that the shuttle may be activated by an air feed-back passage.

Optionally, the treatment compensator may include a stint valve that selectively reduces a flexible passage of the treatment compensator to reduce the first pressure for patient inspiration. The stint valve may include a solenoid actuator controlled by the processor as a function of a measure of pressure from a pressure sensor located proximate to an output of the stint valve. The stint valve may include an actuation lever. Optionally, the lever may be configured proximate to a pressure feedback chamber having a membrane such that the membrane may flex to move the lever with changing pressure of the pressure feedback chamber.

In some cases, the stint valve may include first and second pressure activation chambers adjacent to first and second membranes of the flexible passage. The first pressure activation chamber may be a feed-forward pressure chamber in gas communication with an input side of the flexible passage. The second pressure activation chamber may be a feedback pressure chamber in gas communication with an output side of the flexible passage. The first pressure activation chamber may include a release vent having a release vent gate.

In some cases, a gas source input may be configured to couple with a supplemental oxygen gas source such that the input directs supplemental oxygen to mix with the pressurized air.

Additional features of the present respiratory technology will be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Figure 1:
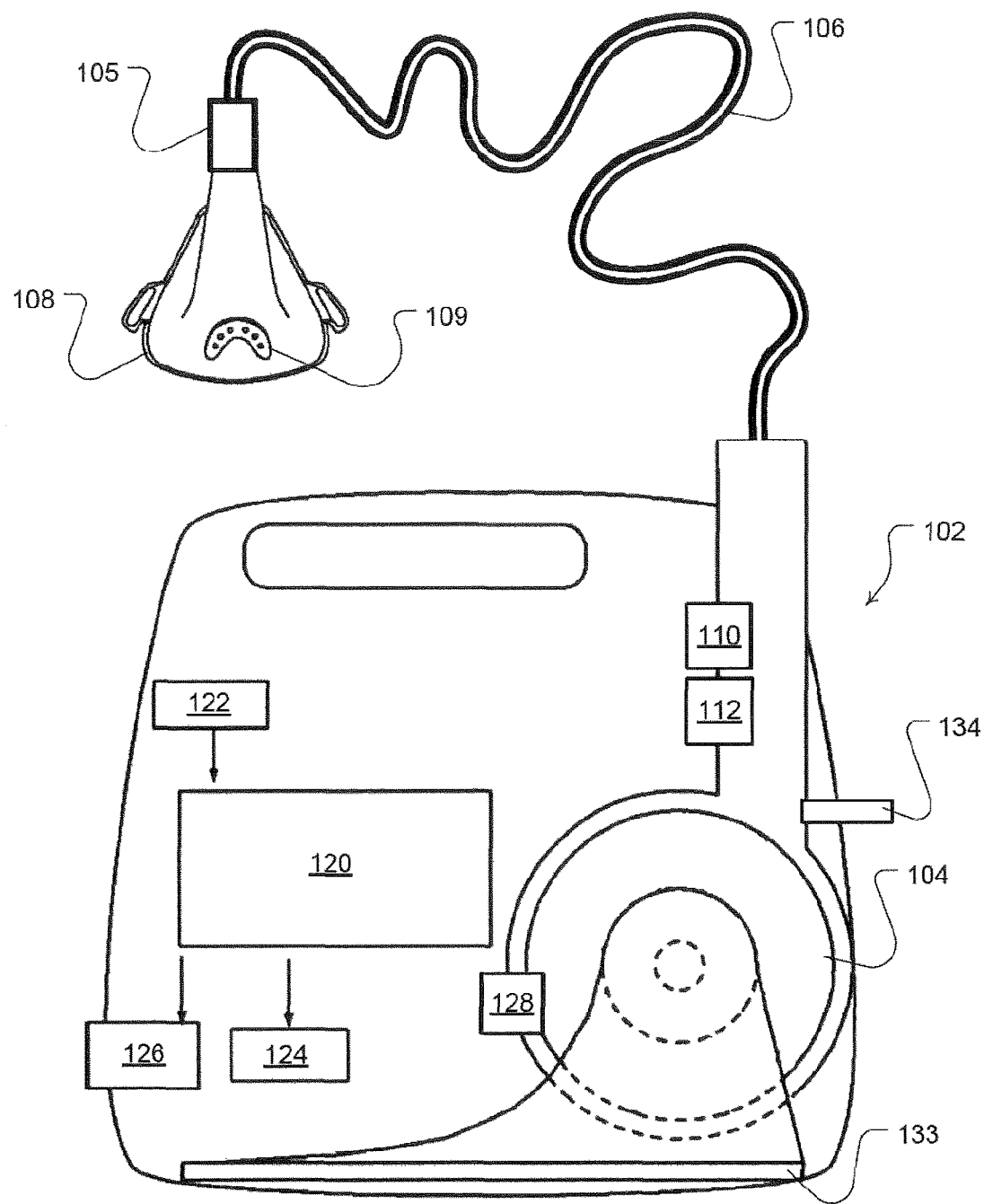
FIG. 1 shows example components of a discreet apparatus for treatment of the airway of a patient of the present technology.
Figure 2:
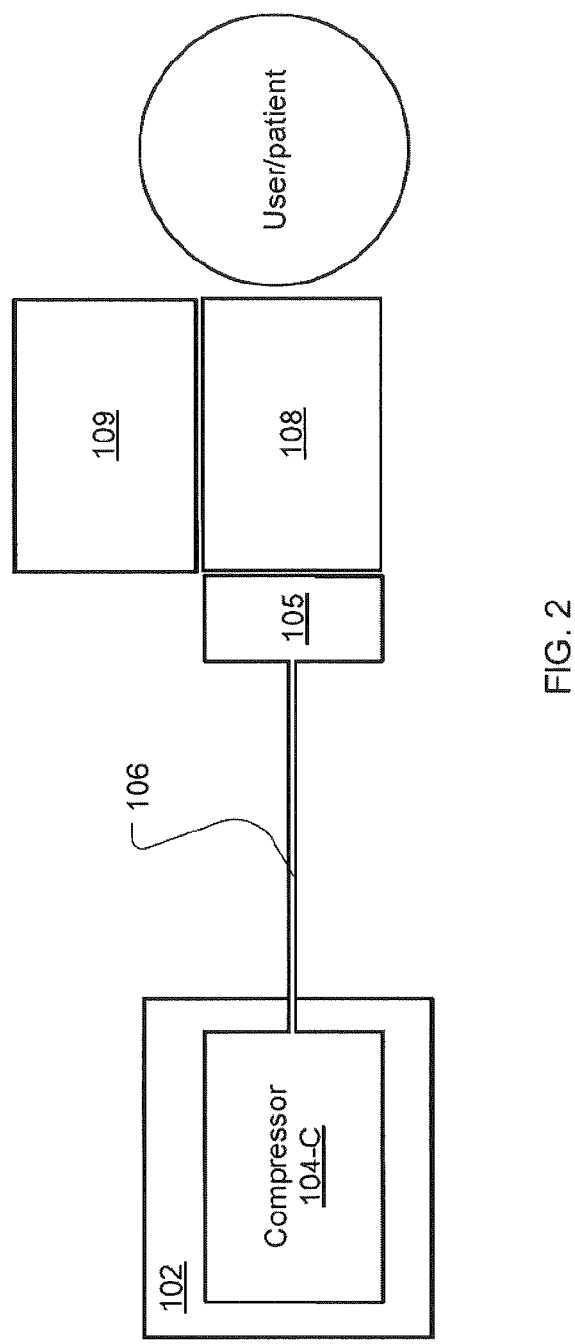
FIG. 2 is a schematic diagram of some of the elements of an example discreet system of the present technology.
Figure 3:
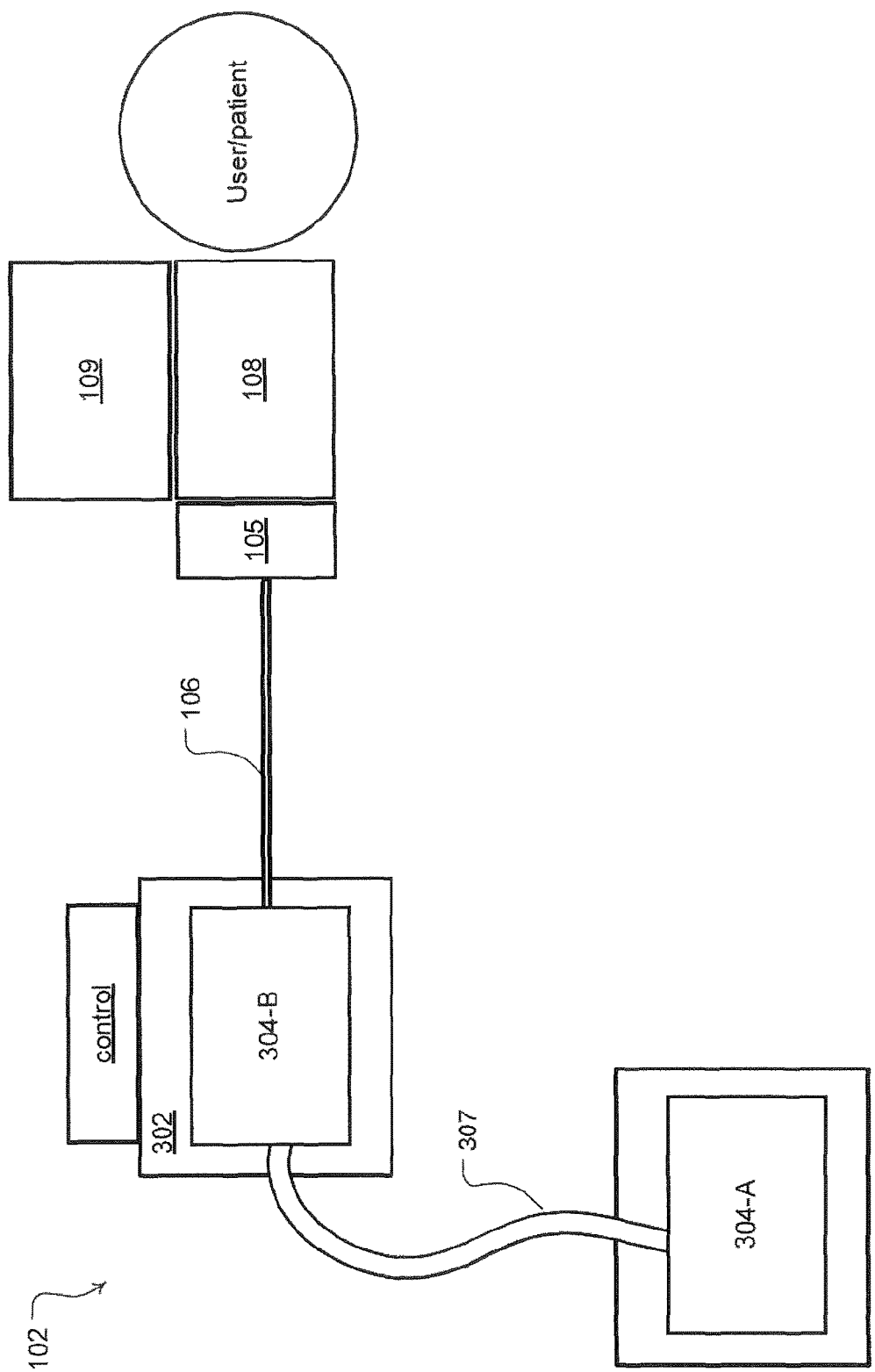
FIG. 3 is a schematic diagram of components of a system of the present technology that employs multiple flow generators.

Embodiments of the present technology may be implemented with an airway treatment device 102 or respiratory apparatus, such as a CPAP, APAP or ventilator apparatus, that may include some or all of the components illustrated in FIGS. 1, 2 and 3. For example, the airway treatment device 102 will typically include flow pressurizer apparatus 104, to generate a flow of air under pressure in a manner that increases the pressure of ambient air drawn in by the pressurizer. Thus, the flow pressurizer apparatus 104 may include an air inlet, which may have an optional filter 133. Optionally, a supplemental gas supply may be introduced through a supplemental gas port 134. Gas from such a distinct gas supply or gas source, such as oxygen, may mix with or supplement the pressurized air that is pressurized by the flow pressurizer apparatus. The airway treatment device 102 will typically include a user interface such as one or more input buttons, switches or key press controls 122 and a display 124, such as a light emitting diode (LED) display or liquid crystal display (LCD). An optional data interface 126 may be provided for wired or wireless data exchange between the controller of the apparatus and external systems.

Controller and Sensors

The airway treatment device 102 will typically include a controller 120, such as one or more processors. The controller may control the generated airway treatment based on signals from one or more optional sensors such a flow sensor 110 and/or a pressure sensor 112. The flow sensor generates a signal representative of the patient's respiratory flow and may include components of any intentional or unintentional leak. For example, flow associated with a nasal cannula or mask may be measured using a pneumotachograph and differential pressure transducer or similar device such as one employing a bundle of tubes or ducts to derive a flow signal f(t). Alternatively, a pressure sensor may be implemented as a flow sensor and a flow signal may be generated based on the changes in pressure. Although the flow sensor 110 is illustrated in a housing of the controller 120, it may optionally be located closer to the patient, such as in the patient interface 108 or an optional sense tube (not shown). Other devices for generating a respiratory flow signal may also be implemented.

One or more pressure sensors 112 may be positioned to provide information concerning the treatment pressure. The sensor may be positioned in various locations of the apparatus, such as in the mask or cannula, at an output of a compressor or blower etc., at or within any intermediary component of the flow path of the system (e.g., proximate to a treatment compensator as described in more detail herein or proximate to an outlet of a fine bore delivery tube.) Each pressure sensor will generate a pressure signal indicative of a pressure level at the location monitored by the sensor.

The signals from the various sensors (when present) may be sent to the controller or processor 120, such as by wired signals or wireless signals (e.g., via Bluetooth transmissions). Optional analog-to-digital (A/D) converters/samplers (not shown separately) may be utilized in the event that supplied signals from the sensors are not in digital form and the controller is a digital controller.

Based on input signals from these sensors and/or other optional sensors, the controller 120 may in turn generate air flow or pressurization control signals. For example, the controller may generate an RPM request signal to control the speed of flow pressurizer apparatus 104 by setting a desired frequency or rotational velocity set point and comparing it with the measured condition of a frequency or velocity sensor 128. Alternatively, such changes may be based on determining a desired flow set point and comparing it with the measured condition of the flow sensor. Alternatively, such changes may be based on determining a desired pressure set point and comparing it with the measured condition of a pressure sensor. Typically, such changes to the motor speed are accomplished by increasing or decreasing supplied motor current with a servo based on determined differences between set and measured conditions such as in a closed loop feedback fashion and translating the difference to current. Thus, the processor or controller 120 may make controlled changes to the treatment delivered to the patient interface from the flow pressurizer apparatus 104.

The controller or processor 120 can typically be configured and adapted to implement particular control methodologies such as the methods described in more detail herein. Thus, the controller may include integrated chips, a memory and/or other control instruction, data or information storage medium. For example, programmed instructions encompassing such a control methodology may be coded on integrated chips in the circuits or memory of the device or such instructions may be loaded as software or firmware using an appropriate medium. With such a controller or processor, the apparatus can be used for many different airway treatment therapies, such as the pressure or flow treatments previously mentioned, by adjusting a pressure delivery equation that is used to set the flow pressurizer apparatus or the exhaust venting by an optional release valve (not shown). Thus, pressure may be controlled at desired levels as set by the switches or a user interface 122 of the device. The pressure may be kept substantially constant over the phases of respiration. In some embodiments, the generated pressure may be kept generally constant over the inspiratory cycle and provide some expiratory relief. Alternately, in some embodiments the pressure may be varied smoothly to replicate the patient's detected respiration cycle.

In some embodiments of the device, indications of upper airway obstruction determined by the controller are servo-controlled by varying the pressure. For example, a device in accordance with the technology may monitor the patient for signs of partial or complete upper airway obstruction, airway resistance, obstructive apnea, obstructive hypopnea, snoring etc. Upon detection of such events, and according to the severity and frequency of such events, the level of pressure is increased. In some embodiments, if the events are no longer detected, the level of pressure may be reduced.

In one embodiment, the controller may determine a tidal volume or other measure of inspired volume of air or gas over time by the patient during treatment. Such a determination may be used for setting the pressure or flow and/or analyzing conditions of the patient's airway or respiration for example, by controlling a pressure support (PS) to satisfy a target ventilation (e.g., a desired volume of air over a period of time).

Patient Interface

The airway treatment device 102 will also typically include a patient interface 108 such as nasal prongs or nasal cannula, nose mask, mouth and nose mask, nasal pillows etc. to direct the flow of air or breathable gas at the airway of a user of the device or a patient. The patient interface may be directly or indirectly coupled with the delivery conduit 106 to receive pressurized air from the conduit. In one form of such a patient interface, exhaust gas of the apparatus and/or expiratory gas from the patient's airway can be vented away from the patient interface with a vent 109, which may be a variable or fixed vent such as any of the vents described in U.S. Provisional Patent Application No. 61/558,158 filed on Sep. 13, 2011, the disclosure of which is incorporated herein by reference.

Breathable Gas Delivery Conduit

In response to the controller 120, the flow pressurizer apparatus 104 may generate varied flows or pressures for a patient treatment. Thus, it may be coupled so as to direct the breathable gas toward a patient interface through a gas delivery conduit 106. Such a conduit may be implemented with a length of fine bore tubing. A "fine bore" conduit may be understood herein to be a conduit having a gas channel with a cross-sectional area on the order of less than about 50 mm$^2$. For example, it may be a conduit having an air passage inside diameter in a range of 2 mm to 8 mm. A further example conduit may be a 7 mm outside diameter ("O.D.") tube or an 8 mm O.D. tube. In some cases, multiple fine bore tubes (e.g., two 8 mm O.D. tubes or two 7 mm O.D. tubes) may serve as the delivery conduit. However, it will be understood that larger bore conduits may be implemented in some embodiments of the present technology. Such larger bore conduits may be, for example, 15 mm or 22 mm O.D. tubing or other low impedance conduit. Since the gas delivery conduit 106 will typically lead to the patient interface 108, for purposes of comfort, the length of such a hose may be one or more meters (e.g., 1 to 6 meters in length) to permit a comfortable distance from the flow pressurizer apparatus 104. In the case where the flow pressurizer apparatus 104 is intended to be wearable or in close proximity to the patient, the length of such a hose may be less than one meter (e.g. 0.7 m or less).

Flow Pressurizer Apparatus

As previously described, the breathable gas for treatment may be controlled to have various flow rates or pressure levels above atmospheric pressure to the patient interface for a patient treatment. Thus, the flow pressurizer apparatus, in response to the controller, may automatically adapt its treatment pressure based on detected conditions (e.g., SDB events like snoring, obstructive apnea, obstructive hypopnea, flow limitation, etc.). Moreover, the apparatus may be configured to produce pressures as a CPAP apparatus, Pressure Support apparatus, bi-level apparatus, APAP apparatus, etc. Such therapy pressures may typically be provided to the patient in the range of 4 to 22 $cmH_2O$ and flows may be in a range of about 10 to about 40 liters/min. However, fine bore conduits have high impedance so can present significant issues in the control of treatment, due to the passage size restriction through which the breathable gas is directed. Thus, conventional flow generation system configurations may not be suitable for such implementations. Accordingly, the present technology may implement a flow pressurizer apparatus, such as with a set of flow generators as illustrated in FIG. 3 or a compressor as illustrated in FIG. 2. Such apparatus may be configured to generate air pressures significantly higher than the level required for patient therapy, and the levels typically provided by conventional devices, so as to overcome the limits (e.g., pressure drop) of the fine bore delivery conduit. Additional components for the airway treatment device 102 of the present technology herein may also be implemented to particularly compensate for restrictions associated with such conduits.

Thus, a flow pressurizer apparatus of the present technology may typically be configured to generate pressures to the fine bore conduit higher than the typical range for treatment of OSA or Pressure Support ventilation depending on the purpose of the device. Thus, a range of pressure generated by such a device may include the typical ranges for CPAP treatment of about 4-22 cm $H_2O$ or a typical range for pressure support treatment of about 4-32 cm $H_20$, but may also be configured to generate additional high pressures exceeding those ranges depending on the different configuration of the delivery conduits (e.g., length and size). Such highly increased pressure at the flow generator may thereby serve to increase the density of the breathable gas to levels that permit the airflow through the fine bore delivery conduit at relatively slow flow rates (e.g., below typical flow rates for such respiratory treatment apparatus). A subsequent reduction in pressure attributable to the treatment compensator at the patient interface may then permit a relatively higher (increased) flow rate (e.g., a more typical flow rate) of the gas to the patient interface as a result of gas expansion at the treatment compensator.

As illustrated in FIG. 2, the flow pressurizer apparatus 104 may include a compressor 104-C. In a typical embodiment, the compressor may include a motor (not shown). The motor may have an array of airfoils such as in an axially compressor configuration. The motor may also have an impeller such as in a radial compressor configuration. Other compressor configurations may also be implemented, such as one based on a piston configuration. The compressor may be configured to generate the pressures necessary to overcome the impedance restrictions of the fine bore delivery conduit.

Alternatively, as illustrated in FIG. 3, the flow pressurizer apparatus 104 may be formed by a set of flow generators 304-A, 304-B. In some such embodiments, the flow generators may be formed by a servo-controlled blower or fixed speed blower. The blower may include a motor with an impeller within a volute. Such a system configuration may include an initial stage flow generator 304-A and a step-up flow generator 304-B. The two flow generators may be coupled by a junction delivery conduit 307, such as a large bore conduit or other low impedance delivery conduit (e.g., 14-22 mm O.D. conduit or greater). The pressurized output flow of air from the initial stage flow generator 304-A is directed through the junction conduit 307 to the input of the blower of the step-up flow generator 304-B. The two flow generators can provide a multi-stage pressurization configuration to provide the necessary pressures to overcome the impedance of the fine bore delivery conduit 106. For example, the initial stage flow generator 304-A may be controlled to dynamically adjust treatment pressure to the different levels of pressurization to treat SDB and/or to change to provide an expiratory pressure relief in synchronization with detected patient respiration while the step-up flow generator 304-B may provide a fixed pressure necessary to overcome the pressure drop associated with the fine bore conduit. Alternatively, the initial stage flow generator 304-A may be configured to provide a fixed level of pressure that may be associated with the pressure drop of the fine bore tube and the step-up flow generator 304-B may be controlled to dynamically adjust the pressure suitable for treatment (e.g., pressure support adjustments, bi-level adjustments, treatment pressure increases for expiratory pressure relief, automatic treatment pressure adjustments (increases or decreases) based on detected sleep disordered breathing events or lack thereof).

In some such embodiments, a controller 120 may be located within the initial stage flow generator 304-A, the step-up flow generator 304-B or both. For example, in some embodiments, the controller 120, as well as the user interface 122 and display 124 may be included in the step-up flow generator 304-B. A user or patient may then operate both flow generators by setting the controls of the step-up flow generator 304-B. In some such examples, the flow generator 304-B may have a small or mini size so as to be capable of placement on the patient's bed side table. The flow generator 304-A may be sized to be positioned under the patient's bed or otherwise out of sight. The flow generator 304-A may supply constant air to mini flow generator 304-B by for example, a 15 mm or 22 mm tube, or tube with low impedance. The mini flow generator 304-B may receive data from a sensor located on the patient interface 108 or mask. For example, the sensor may receive the pressure of the air at the mask. Based on the data from the sensor, mini flow generator 304-B may adjust the flow and/or pressure to the mask to ensure the patient is receiving a constant pressure at the mask. Mini flow generator 304-B may then be connected to the mask by a fine bore tube (e.g., a tube in the range of 6-9 mm, such as a 7 mm tube).

In some embodiments, the patient or user can control the system by buttons or other user controls on the mini flow generator 304-B as this may be in a convenient location. Of course, in some embodiments, all of the controls may be on the other flow generator 304-A. Alternatively, some controls may be positioned on the mini flow generator 304-B (such as frequently used controls for humidification and temperature (i.e., when a humidifier and water and/or tube heaters are implemented with any of the flow generators), and on-off switching) and other controls may be on the flow generator 304-A. In some such cases, a bus or interface may be provided for purposes of data communication between the flow generators.

In some versions of the configuration of FIG. 3, the initial stage flow generator 304-A can be implemented by a powerful and/or large footprint flow generator capable of generating the highest pressures as required to meet the pressure levels described herein to overcome the impedance issues of the fine bore tube. In such a case, the initial stage flow generator 304-A provides the high pressure to the flow generator 304-B via the junction delivery conduit 307. In this case, the flow generator 304-B may be configured to regulate or control regulation of the patient's pressure requirements to the high pressure input side of a treatment compensator that is described in more detail herein. This will permit the treatment compensator to be supplied with an ample reservoir of pressure at the treatment compensator's high pressure input side to allow the treatment compensator to satisfy the patient's pressure requirements at the low pressure output side of the treatment compensator so as to supply a suitable pressure to the patient or patient interface.

Treatment Pressure Compensation

Accordingly, some embodiments of the present technology may implement a treatment compensator, such as treatment compensator 105 located at or near the patient interface. The treatment compensator is configured to reduce the high pressures of the air treatment emanating from the fine bore delivery conduit 106 so that the output levels of pressure may be lowered to be suitable for inspiration by the user or patient with the patient interface for the pressure treatments described herein. Thus, in a typical embodiment, an air or breathable gas input to the treatment compensator 105 will be from an output of the fine bore conduit 106 and an output of the treatment compensator will lead to an input of the patient interface 108. Examples of such apparatus may be considered in reference to FIGS. 4 through 10.

Figure 4:
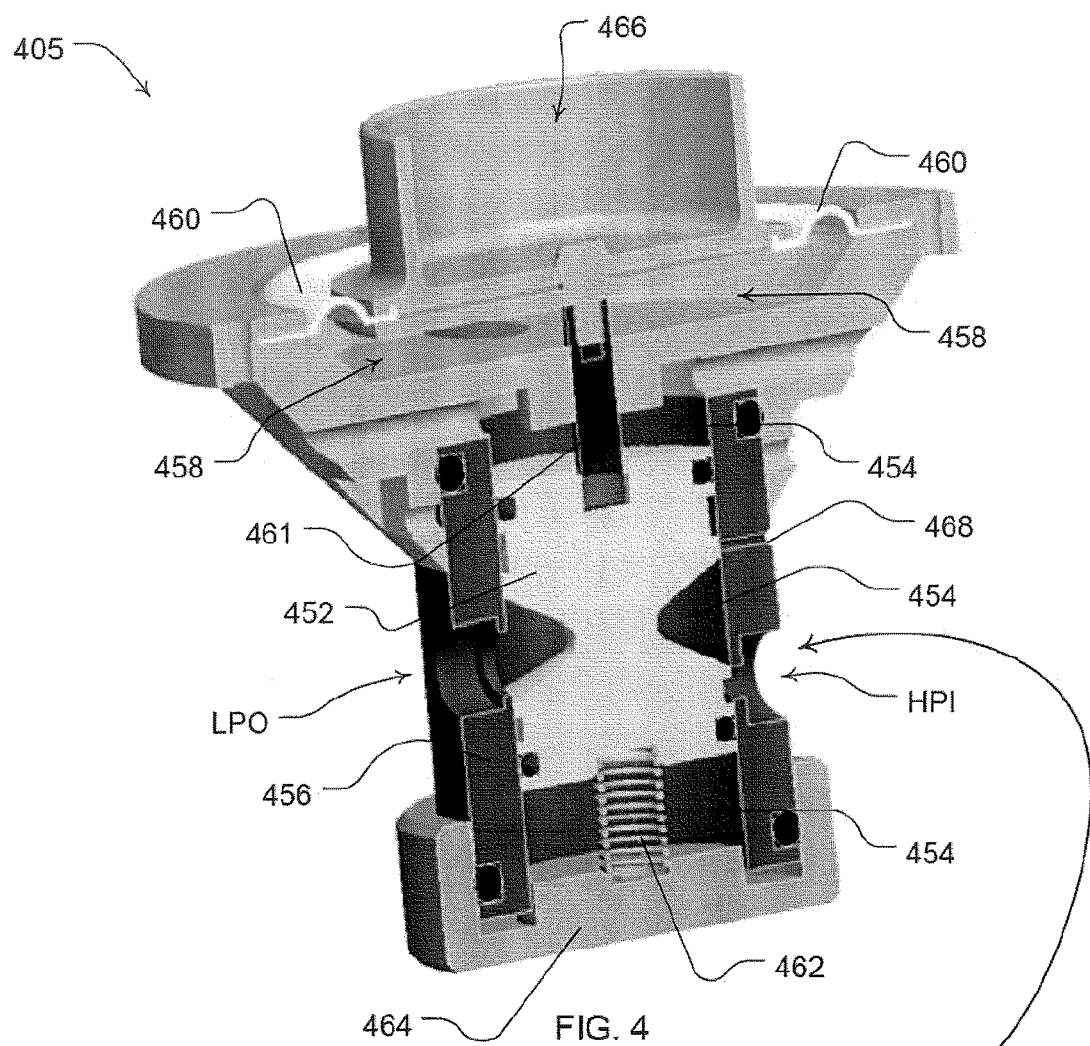
FIG. 4 is a cross sectional illustration of a treatment compensator in some embodiments of the present technology.
Figure 4A:
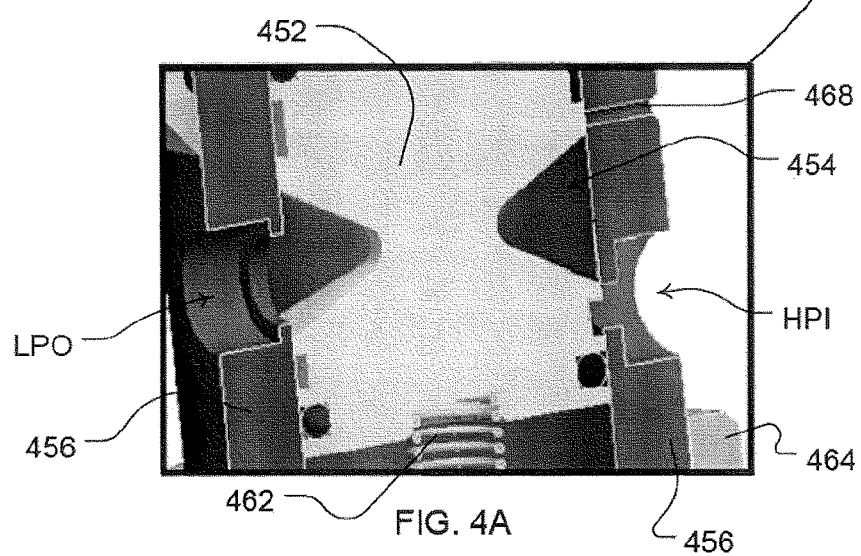
FIG. 4A is a cross section illustration of a portion of the treatment compensator of FIG. 4.

The treatment compensator 405 in the example of FIGS. 4 and 4A includes a mechanical shuttle 452, such as one with an hourglass shape that provides a central area for gas passage. The shuttle may move within a shuttle chamber 454 that may be formed by a cylinder 456. The cylinder 456 includes a high pressure input HPI, such as from an output of a fine bore conduit 106, and a low pressure output LPO, such as for providing treatment pressure to the patient interface or mask. Operational movement of the shuttle permits a step down or reduction of the pressure within the chamber 454 with respect to the high pressure input. In this regard, movement of the shuttle permits a greater or lesser size of an opening of the high pressure input HPI to the shuttle chamber 454.

Movement of the shuttle may be controlled by pressure in a control chamber 458. The control chamber 458 may expand and contract with pressure in accordance with a pressure of the low pressure output LPO that is directed to the control chamber 458 by a feedback passage (not shown) from the low pressure output to the control chamber 458. A control chamber diaphragm 460 permits expansion and contraction of the chamber. A shuttle rod 461 couples the shuttle and control chamber top 466 to permit a complementary movement of the top of the control chamber and the shuttle when the control chamber expands or contracts.

The shuttle may be biased by one or more biasing elements that provide biasing forces. Such biasing forces may serve to adjust the response of the shuttle to pressure in the control chamber 458 such that the compensator may be configured to reduce the high pressure to a desired degree such as to permit a fixed step down in pressure from the high pressure input side to the low pressure output side. For example, a shuttle spring 462 may be implemented between a base side of the shuttle and a base cap 464 of the cylinder 456. Similarly, a weight or other spring element may be applied at the control chamber top 466. Optionally, one or more of such biasing elements may be adjustable so as to permit adjustment of the force for or during use. For example, a screw may be implemented to increase or decrease a biasing force of a spring applied at the top. Optionally, an electro-mechanical actuator, such as a stepper motor having a threaded rod coupled to rotate with the rotor, may be implemented for automated controlled adjustments to the biasing force at the top 466. A bleed passage or opening 468 from the shuttle chamber to atmosphere may be provided to permit an escape of air or gas that may be trapped in the shuttle chamber.

Figure 5:
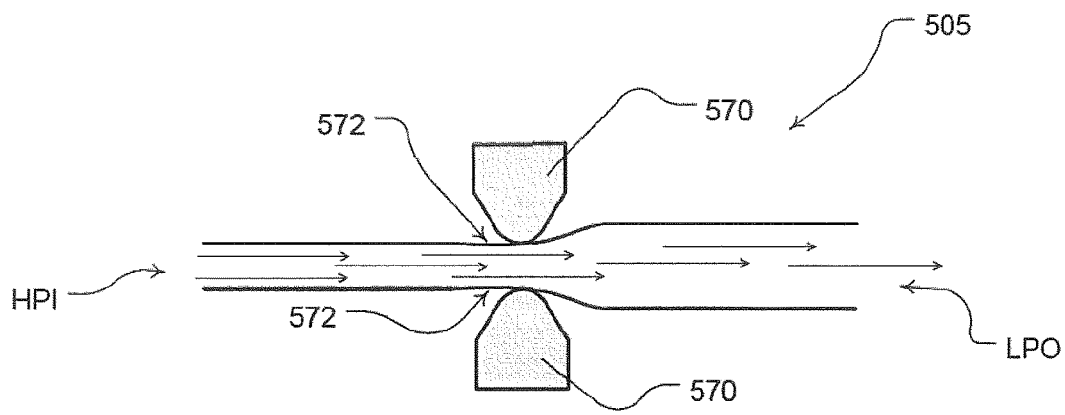
FIGS. 5 and 6 illustrate operation of a stint valve version of a treatment compensator in some embodiments of the present technology.
Figure 6:
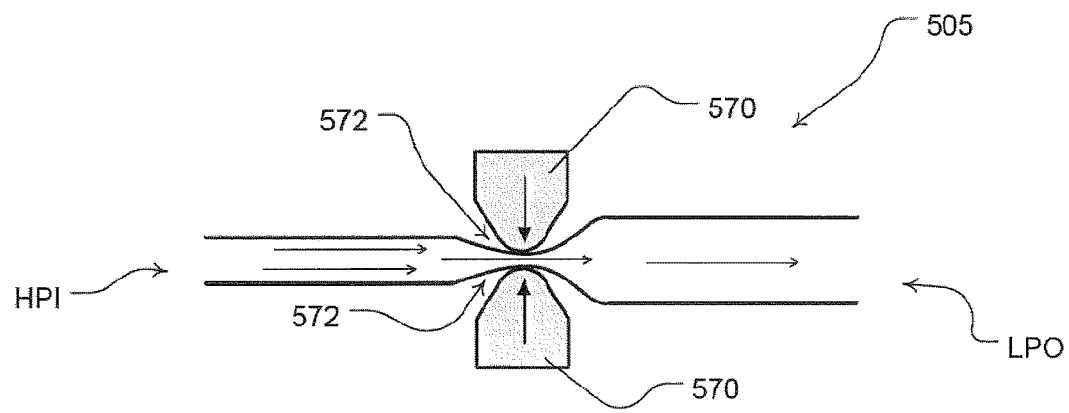

The treatment compensator 505 in the examples of FIGS. 5 and 6 may be configured as a stint valve. The stint valve may include one or more pinch elements 570. The pinch elements 570 may be configured to ply a force against a flexible portion 572 of a passage of the valve. For example, as illustrated in FIG. 6, a movement force of one or more of the pinch elements may constrict an opening of the passage of the valve with the flexible portion 572. As a result, a step down in pressure from a high pressure input HPI side and a low pressure output LPO side may be achieved. In such a case, the low pressure input side may be coupled with a fine bore conduit 106 as previously described while the low pressure output side may be coupled with a patient interface 108.

Figure 7:
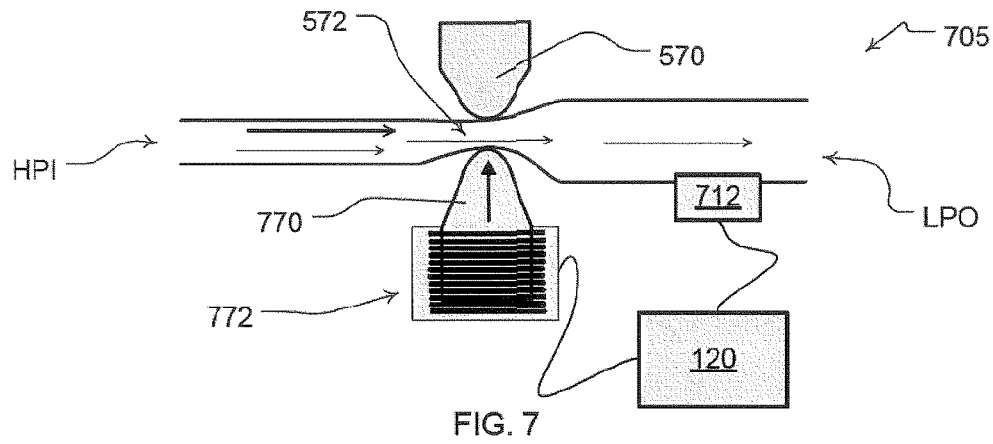
FIG. 7 is a cross sectional view of an electro-mechanical treatment compensator.

While the stint valve may be manually set for a fixed step down of pressure, some embodiments may be implemented to provide automated control for dynamically setting the restriction of the stint valve and thereby dynamically setting the step down in pressure. Some examples are illustrated with reference to the treatment compensator 705, 805 of FIGS. 7 and 8 respectively. In FIG. 7, one or more of the pinch elements 570 may be formed by an actuator, such as an electro-mechanical actuator. For example, the stint valve may include a solenoid 772 as a pinch element. The solenoid, including one or more field coils, may be controlled by a controller or processor, such as controller 120 so as to change a position of its pinch element 770 and thereby selectively increase or decrease the passage size of the valve. The controller may be responsive to changes in measured pressure detected by a pressure sensor 712. In such a case, the pressure sensor may be located to measure pressure within a gas passage of the low pressure output LPO of the stint valve. When only one pinch element is configured for movement, the opposing pinch element 570 may serve as a stop.

Figure 8:
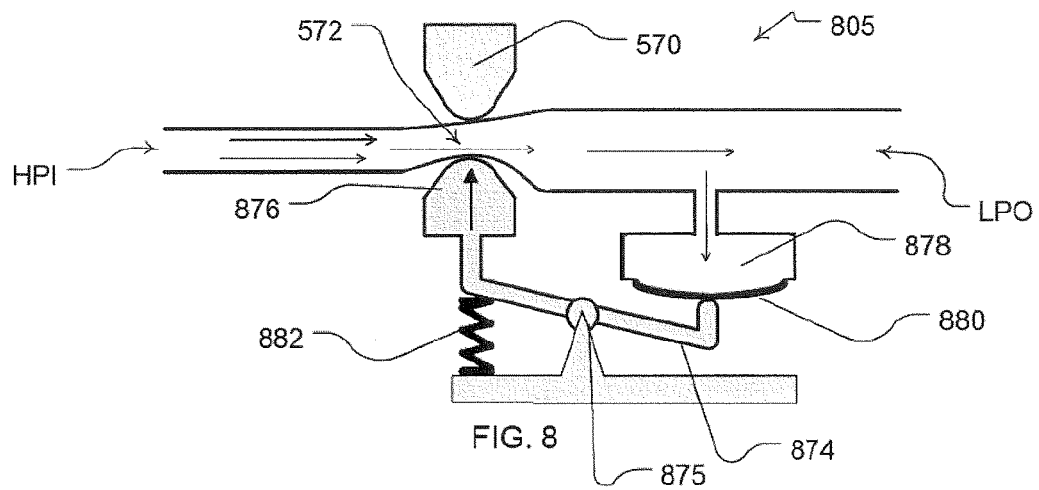
FIG. 8 is a cross sectional view of an pneumatic-mechanical treatment compensator.

In some embodiments, the stint valve may be dynamically adjusted by pneumatic forces. For example, as illustrated in FIG. 8, the stint valve may include a lever 874, such as one on a pivot 875. The pinch element 876 may be a portion of the lever 874 or coupled therewith. A lever activation chamber 878 such as one providing a feed-back pressure from a low pressure output of the stint valve may serve to actuate the lever by expansion or contraction of a flexible membrane 880 of the chamber in contact with the lever. Optionally, the lever may be biased, such as by a lever spring 882. Setting of the force of the lever spring may set a preload on the lever to change the set step down of pressure of the valve. Expansion of the chamber 878 with increasing pressure of the low pressure output side LPO may then serve to pinch the stint valve to decrease the passage of the stint valve and thereby decrease the pressure of the low pressure output side LPO. Contraction of the chamber 878 with decreasing pressure of the low pressure output side LPO may then serve to open the stint valve to increase the passage of the stint valve and thereby increase the pressure of the low pressure output side LPO of the valve.

Figure 9:
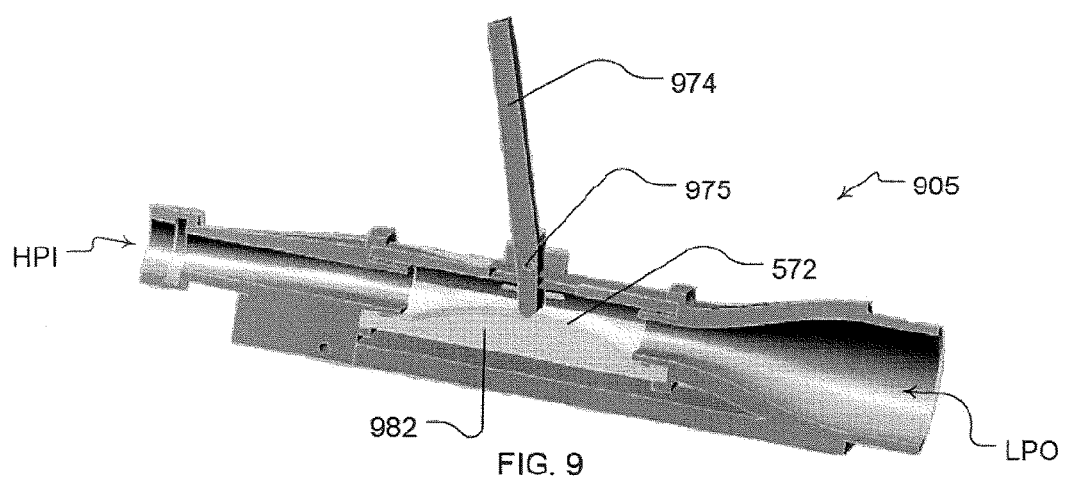
FIG. 9 is a cross-sectional perspective view of another example of a treatment compensator suitable for some embodiments of the technology.

In the example of FIG. 9, the stint valve of the treatment compensator 905 includes a flexible passage 572 between the high pressure input HPI side and the low pressure output LPO side that is formed by a flexibly resilient cushion 982. The cushion may be in contact with a cushion actuation lever 974 that may swing on a pivot 975. Movement of the lever in one direction may compress the cushion to increase the passage size of the valve. Movement of the lever in an opposite direction may release the cushion from the force of the lever so that the cushion may resiliently expand to reduce the size of the flexible passage. In this way, the size of the flexible passage may be varied to selectively increase or decrease the step down of pressure between the input and output sides of the valve. Optionally, the lever may be actuated by various components. For example, it may be coupled with a solenoid or a screw drive motor to change the position of the lever.

Figure 10:
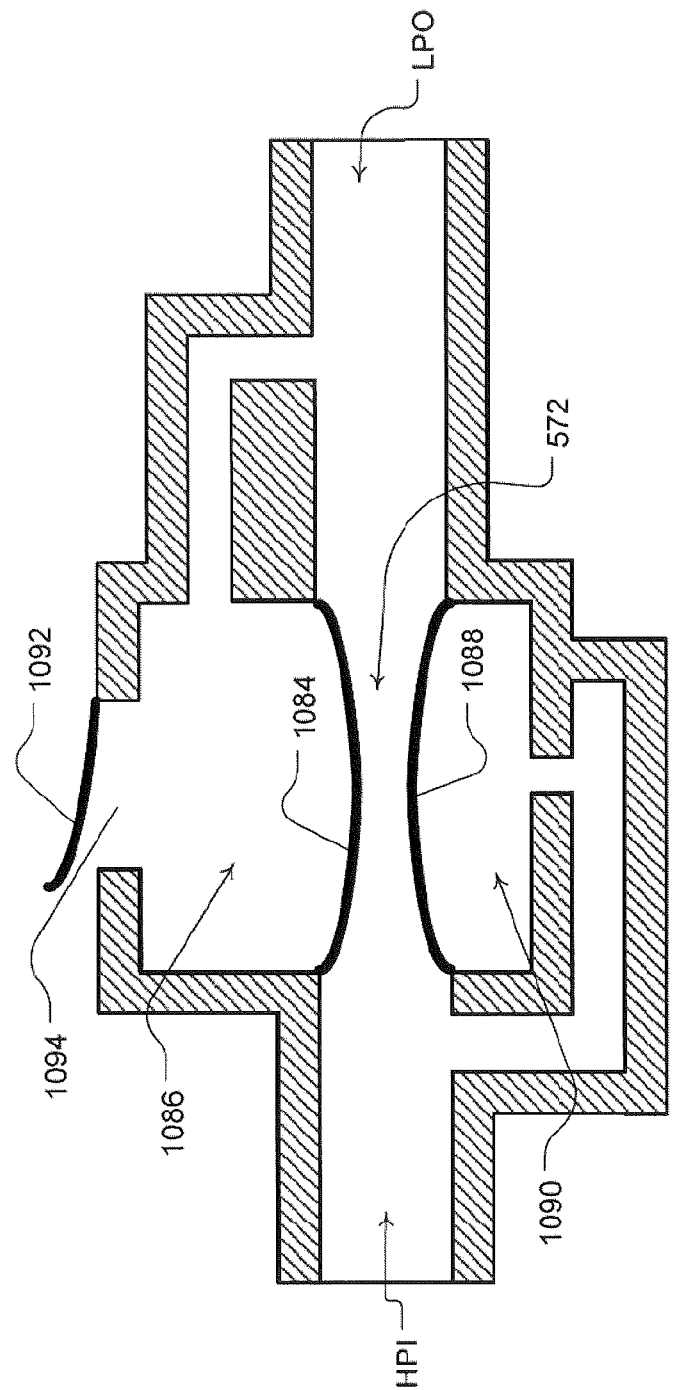
FIG. 10 is an illustration of an example pneumatic valve treatment compensator that may be employed in some embodiments.

In the example treatment compensator of FIG. 10, pneumatic control also serves to adjust the passage size of the stint valve between the high pressure input HPI side and the low pressure output LPO side. In this version, no pinch elements are employed. Rather, constriction and expansion of the flexible portion 572 of the valve is achieved with multiple pressure chambers, such as a pressure feed-back chamber and a pressure feed-forward chamber. In this embodiment, a flexible membrane 1084 of a pressure feedback chamber 1086 forms the flexible portion 572 of the valve. Similarly, the flexible membrane 1088 of a pressure feed-forward chamber 1090 also forms the flexible portion 572 of the valve. Optionally, the pressure feed-back chamber 1086 may include a release vent gate 1092 for a release vent 1094 opening. Pressure of the high pressure input side of the valve serves to adjust expansion or contraction of the membrane 1088 of the pressure feed-forward chamber 1090. Similarly, pressure of the low pressure output side of the valve serves to adjust the membrane 1084 of the pressure feedback chamber 1086. The release vent gate may be biased to open and release pressure of the feedback chamber in event of an increased pressure condition in the pressure feedback chamber 1086. The balancing of pressure forces of the chamber may permit a controlled compensation of the step down of pressure in the valve from the high pressure input HPI side to the low pressure output LPO side.

Venturi Chamber

Figure 11:
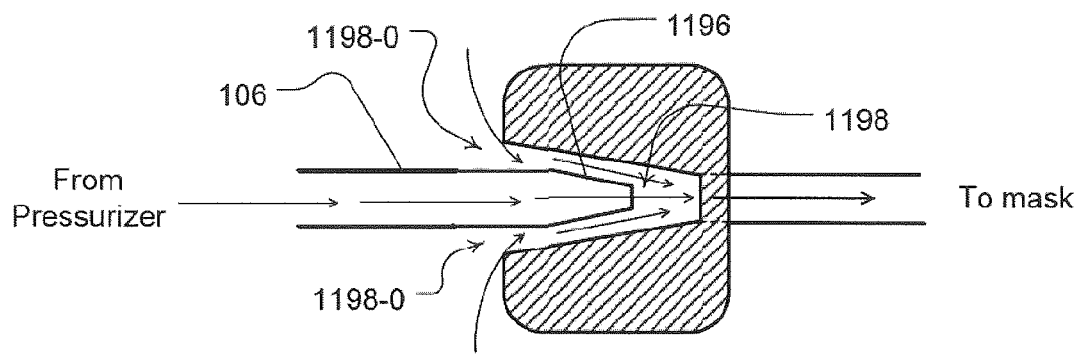
FIG. 11 is a cross-sectional perspective view of an example Venturi coupler for a fine bore delivery conduit of the present technology.

Some embodiments of the present technology may employ a Venturi chamber. Examples of such a feature may be considered in reference to the illustrations of FIGS. 11 and 12. Such a feature may permit an increase in the air supplied to a patient when a fine bore delivery conduit 106 is employed. Thus, the chamber may be implemented as a coupler for a fine bore delivery tube and/or a patient interface. For example, the fine bore conduit 106 may direct a flow of high pressure air to a nozzle 1196 having a tapered end. The nozzle may be positioned within or coupled to the Venturi chamber 1198 so as to have a gap of the chamber surrounding portions of the nozzle. The gap(s) of the chamber lead to a chamber opening 1198-O to atmosphere. During operation, the high pressure flow, accelerated by the taper of the nozzle, may entrain air from atmosphere into the Venturi chamber through the chamber openings 1198-O so as to increase the quantity of air entering the chamber and thereby increasing the air flowing toward a patient for treatment. Optionally, a foam filter 1199 may cover the chamber openings 1198-O to filter air and/or reduce noise at the openings (see FIG. 12).

Figure 12:
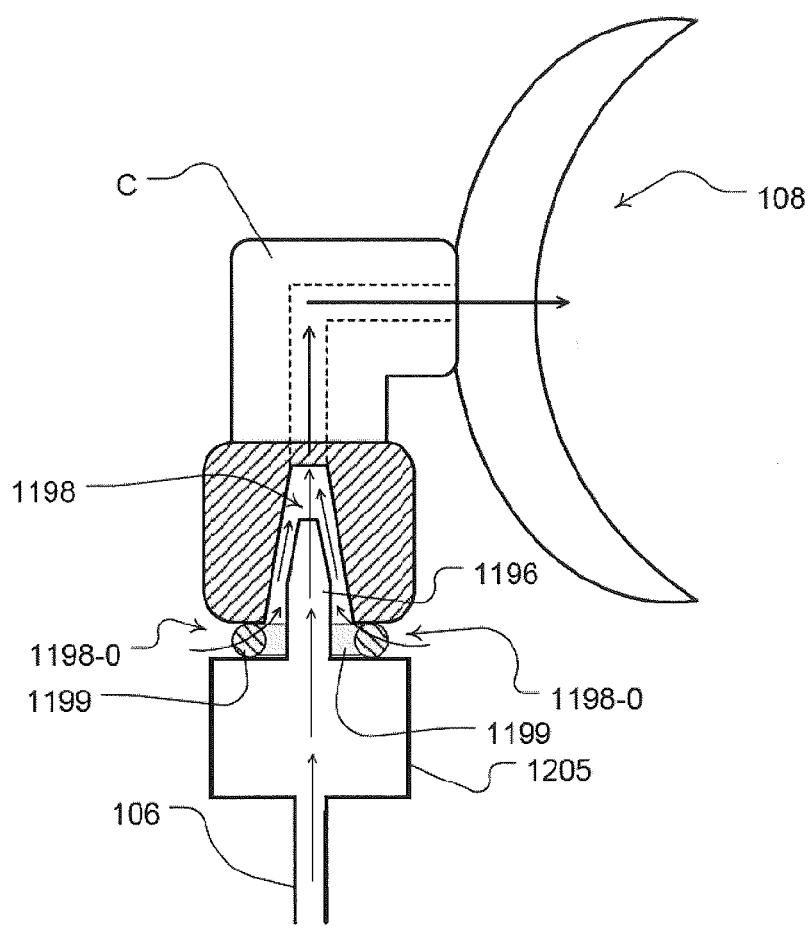
FIG. 12 is another cross-sectional illustration of an example Venturi coupler with a patient interface.

As illustrated in FIG. 12, the Venturi chamber may be coupled to an input of a patient interface 108, such as a mask. An optional swivel and/or elbow connector C may also be employed. Thus, an output of the Venturi chamber may lead to the input of a patient interface or otherwise form a part of the patient interface. In some such cases, a treatment compensator 1205, such as any one of the examples previously described, may optionally be coupled with the nozzle of the Venturi chamber such that the output of the compensator enters the nozzle. Such components may be coupled together with connector or they may otherwise be integrated as a unit.

Further Example Implementation of the Technology

In an example implementation of the aforementioned technology, a pressure treatment system may be configured with the following components:

1. Air compressor—The initial stage flow generator may be implemented as an air compressor. The device may thus be configured to pressurize the required amount of air per minute and supply it to the junction delivery conduit.

2. High pressure air regulator—The step up flow generator device may be configured to regulate the pressurized air entering the fine bore delivery conduit to a more accurate pressure and flow. In such a case, the step up device regulates the flow through the fine bore delivery conduit.

3. Treatment Compensator—This device then reduces the pressure exiting the fine bore delivery conduit to a therapy level of between 2-50 cm $H_2O$, which can be delivered to the patient. It may also regulate the delivery of this pressure to the patient according to the patient's breathing cycle.

Any of the functions mentioned above can be implemented in any other device as desired. Devices may be combined or split up according to any design requirement.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

The invention claimed is:

1. A respiratory treatment system comprising:
   a flow pressurizer apparatus configured to generate a pressurized flow of air through a fine bore delivery conduit toward a patient interface;
   a treatment compensator coupled with the fine bore delivery conduit at the patient interface and configured to reduce a first pressure from the fine bore delivery conduit to a second pressure for delivery to a patient from the treatment compensator, the second pressure being above atmospheric pressure; and
   a processor configured to control adjustments to the first pressure generated by the flow pressurizer apparatus, wherein the flow pressurizer apparatus comprises a first flow generator and second flow generator, each flow generator comprising a motor with impeller and volute, wherein the first flow generator is configured to generate a fixed pressure to overcome pressure drop introduced by the fine bore delivery conduit, and wherein the second flow generator is configured to dynamically generate treatment pressure to different levels of pressurization above the fixed pressure.

2. The respiratory treatment system of claim 1 wherein the second flow generator comprises a controller to control operation of the second flow generator and to control operation of the first flow generator.

3. The respiratory treatment system of claim 2 wherein the first flow generator is coupled with the second flow generator by a large bore delivery conduit.

4. The respiratory treatment system of claim 1 further comprising a Venturi chamber coupled to the patient interface, the Venturi chamber configured to entrain atmospheric air proximate to a nozzle coupled with an output of the fine bore delivery conduit.

5. The respiratory treatment system of claim 4 further comprising a foam filter configured at an entrainment inlet of the Venturi chamber.

6. The respiratory treatment system of claim 1 wherein the treatment compensator comprises a pressure step-down chamber including a shuttle configured to move to reduce the first pressure at an input to the step-down chamber to the second pressure at an output of the step-down chamber, the shuttle activated by an air feed-back passage.

7. The respiratory treatment system of claim 1 wherein the treatment compensator comprises a stint valve configured to selectively reduce a flexible passage of the treatment compensator to reduce the first pressure for patient inspiration.

8. The respiratory treatment system of claim 7 wherein the stint valve comprises a solenoid actuator controlled by the processor as a function of a measure of pressure from a pressure sensor located proximate to an output of the stint valve.

9. The respiratory treatment system of claim 7 wherein the stint valve comprises an actuation lever.

10. The respiratory treatment system of claim 9 wherein the lever is configured proximate to a pressure feedback chamber having a membrane, the membrane being configured to move the lever with changing pressure of the pressure feedback chamber.

11. The respiratory treatment system of claim 7 wherein the stint valve comprises first and second pressure activation chambers adjacent to first and second membranes of the flexible passage, the first pressure activation chamber comprising a feed-forward pressure chamber in gas communication with an input side of the flexible passage, the second pressure activation chamber comprising a feedback pressure chamber in gas communication with an output side of the flexible passage.

12. The respiratory treatment system of claim 11 wherein the first pressure activation chamber includes a release vent having a release vent gate.

13. The respiratory treatment system of claim 1 further comprising a gas source input configured to couple with a supplemental oxygen gas source, the input to direct the supplemental oxygen to mix with the pressurized air.

14. The respiratory treatment system of claim 1 where the treatment compensator is configured to deliver the reduced second pressure above atmospheric pressure to the patient interface during patient inspiration.

15. A respiratory treatment system of claim 1 wherein the treatment compensator includes a shuttle.

16. A method for control of a respiratory treatment apparatus, the method comprising:
producing with a flow pressurizer system a flow of air through a fine bore delivery conduit toward a patient interface at a first pressure above atmospheric pressure;
compensating at the patient interface with a treatment compensator to reduce the first pressure to a second pressure for delivery to a patient from the treatment compensator, the second pressure being above atmospheric pressure; and
with a processor, controlling adjustments to the first pressure generated by the flow pressurizer system,
wherein the flow pressurizer system comprises a first flow generator and second flow generator, each flow generator comprising a motor with impeller and volute, wherein the first flow generator is configured to generate a fixed pressure to overcome pressure drop introduced by the fine bore delivery conduit, and wherein the second flow generator is configured to dynamically generate treatment pressure to different levels of pressurization above the fixed pressure.

17. The method of claim 16 wherein the a controller of the second flow generator controls operation of the second flow generator and the first flow generator.

18. The method of claim 17 wherein the second flow generator is coupled with the first flow generator by a large bore delivery conduit.

19. The method of claim 16 further comprising entraining atmospheric air with a Venturi chamber coupled to the patient interface, the entraining proximate to a nozzle coupled with an output of the fine bore delivery conduit.

20. The method of claim 19 wherein the entraining is performed through a foam filter configured at an entrainment inlet of the Venturi chamber.

21. The method of claim 16 wherein the treatment compensator comprises a pressure step-down chamber including a shuttle moving to reduce the first pressure at an input to the step-down chamber to the second pressure at an output of the step-down chamber, the shuttle activated by an air feed-back passage.

22. The method of claim 16 wherein the treatment compensator comprises a stint valve that selectively reduces a flexible passage of the treatment compensator to reduce the first pressure for patient inspiration.

23. The method of claim 22 wherein the stint valve comprises a solenoid actuator controlled by the processor as a function of a measure of pressure from a pressure sensor located proximate to an output of the stint valve.

24. The method of claim 22 wherein the stint valve comprises an actuation lever.

25. The method of claim 24 wherein the lever is configured proximate to a pressure feedback chamber having a membrane, the membrane flexing to move the lever with changing pressure of the pressure feedback chamber.

26. The method of claim 22 wherein the stint valve comprises first and second pressure activation chambers adjacent to first and second membranes of the flexible passage, the first pressure activation chamber comprising a feed-forward pressure chamber in gas communication with an input side of the flexible passage, the second pressure activation chamber comprising a feedback pressure chamber in gas communication with an output side of the flexible passage.

27. The method of claim 26 wherein the first pressure activation chamber includes a release vent having a release vent gate.

28. The method of claim 16 further comprising a gas source input configured to couple with a supplemental oxygen gas source, the input directing the supplemental oxygen to mix with the pressurized air.

29. The method of claim 16 where the treatment compensator delivers the reduced second pressure above atmospheric pressure to the patient interface during patient inspiration.

30. The method of claim 16 wherein the treatment compensator includes a shuttle.

\* \* \* \* \*